(12) United States Patent
Fischer et al.

(10) Patent No.: US 8,768,501 B2
(45) Date of Patent: Jul. 1, 2014

(54) MAGNETIC NANOSTRUCTURED PROPELLERS

(75) Inventors: Peer Fischer, Freiburg (DE); Ambarish Ghosh, Bangalore (IN)

(73) Assignee: Max-Planck-Gesellschaft zur Foerderung der Wissenscaften e.V. (MPG), Munich (DE)

( * ) Notice: Subject to any disclaimer, the term of this patent is extended or adjusted under 35 U.S.C. 154(b) by 487 days.

(21) Appl. No.: 13/098,126

(22) Filed: Apr. 29, 2011

(65) Prior Publication Data

US 2011/0270434 A1    Nov. 3, 2011

Related U.S. Application Data

(60) Provisional application No. 61/330,364, filed on May 2, 2010.

(51) Int. Cl.
*G06F 19/00* (2011.01)
*B82Y 25/00* (2011.01)

(52) U.S. Cl.
USPC .......................... 700/117; 977/891; 977/904

(58) Field of Classification Search
None
See application file for complete search history.

(56) References Cited

U.S. PATENT DOCUMENTS

| | | | | |
|---|---|---|---|---|
| 5,866,204 | A * | 2/1999 | Robbie et al. | 427/256 |
| 6,206,065 | B1 * | 3/2001 | Robbie et al. | 156/349 |
| 6,248,422 | B1 * | 6/2001 | Robbie et al. | 428/119 |
| 7,106,918 | B2 * | 9/2006 | Bita et al. | 385/6 |

OTHER PUBLICATIONS

Ishiyama et al. "Swimming micro-machine driven by magnetic torque" Sensors and Actuators A 91, pp. 141-144, 2001.*
Singh et al. "Metal-coated Si springs: Nanoelectromechanical actuators" Applied Physics Letters vol. 84, No. 18 pp. 3657-3659; May 2004.*
Zhang et al. "Artifical bacterial flagella: Fabrication and magnetic control" Applied Physics Letters 94, 3 pp. 064107-1 to 064107-3, Feb. 2009.*
Zhang et al. "Characterizing the Swimming Properties of Artificial Bacterial Flagella" Nano Letters vol. 9, No. 10, pp. 3663-3667,2009.*
Zhao et al. "Designing Nanostructures by Glancing Angle Deposition" Proceedings of Spie vol. 5219; pp. 59-73; Oct. 2003.*

* cited by examiner

*Primary Examiner* — Sean Shechtman
*Assistant Examiner* — Steven Garland
(74) *Attorney, Agent, or Firm* — Edwards Wildman Palmer LLP; Peter F. Corless; Steven M. Jensen (57) ABSTRACT

Methods and systems for the fabrication and application of Magnetically Actuated Propellers (MAPs) are described. MAPs are structures with typical feature sizes in the range of 20 nanometers up to 100 microns in one spatial dimension. MAPs are propellers that can be obtained from nano-structured surfaces and that can be produced in large numbers. MAPs are propelled and controlled by magnetic fields. The MAPs are optimized for low Reynolds number propulsion and can be moved in fluids and biological tissues. MAPs are useful for measurements, quantification, imaging and sensing purposes e.g. detecting biomolecules and for the controlled transportation of (drug- and bio-) molecules and the delivery of microscopic and nanoscale objects and/or materials or systems of therapeutic value. The MAPs are formed on a substrate and the released from the substrate using sonication, vibration, agitation, dissolution or etching which allows the MAPs to be produced in large numbers.

24 Claims, 10 Drawing Sheets

MAGNETIC NANOSTRUCTURED PROPELLERS

CROSS-REFERENCE TO RELATED APPLICATIONS

This application claims the benefit of priority to U.S. Provisional Application 61/330,364, filed May 2, 2010, the entirety of which is hereby expressly incorporated by reference.

BACKGROUND OF THE INVENTION

1. Field of the Invention

The invention relates to a system and method of preparing Magnetically Actuated Propellers (MAPs) that can be propelled and controlled by magnetic fields for biomedical and rheological applications. The disclosed method, in particular, describes structures which can be produced with typical feature sizes that range in one dimension from more than 20 nanometers to sizes that are below 100 microns in all dimensions. The propellers are made from nano-structured surfaces and can be produced in large numbers.

The invention further describes a propulsion method that uses magnetic fields in order to control and propel MAPs in solutions, suspensions, liquids, and tissue and other soft matter.

2. Description of the Related Art

There is a great interest in the fabrication of structures whose motion can be controlled in liquids or soft matter or tissue or suspensions. There is a need to be able to build and propel artificial robotic swimmers that rival the versatility of biological swimmers of similar size, such as those of motile bacterial cells. Applications for artificial swimmers range from use in complex fluids to diagnostics and targeted drug delivery to microsurgery. It is necessary that the motion of these structures—that are referred to with a number of descriptions, such as "artificial swimmers", "artificial bacteria", "propellers", "micro-bots", "nano-bots", etc.—can be made in large numbers and that they can be controlled from a distance and that they can be steered and propelled by a convenient means.

While significant progress has been made in making larger scale objects that can be manipulated in liquids, the difficulty of attaining a high level of control for smaller devices (<mm) is far from trivial, since obtaining any motion at small length scales requires special strategies. The problem has for instance been described by Purcell (E. M. Purcell, "Life at low Reynolds number," Am. J. Phys. 45, 3-11 (1977)), who described how microorganisms, such as bacteria and spermatozoa achieve locomotion by screw-like and flexible oar-like (non-reciprocal) movements, respectively. The difficulty lies in the fact that the motion of small objects, such as those that are detailed in this invention, is dominated by viscous drag forces (while glide and lift is absent). Low Reynolds number hydrodynamics is described in J. Happel and H. Brenner, Low Reynolds Number Hydrodynamics. (Prentice-Hall, Englewood Cliffs, N.J., 1965). The structures and/or their propulsion method therefore need to permit motion under conditions of low Reynolds number hydrodynamics.

To propel artificial micro- and nano-scale objects, a variety of sources of power, such as electric fields, chemical reactions, and optical forces etc. have been used (Wang Joseph and Manesh Kalayil Manian, "Motion Control at the Nanoscale," Small 6 (3), 338-345 (2010); Stephen Ebbens and Jonathan Howse, "In pursuit of propulsion at the nanoscale," Soft Matter (2010); Mirkovic Tihana, S. Zacharia Nicole, D. Scholes Gregory et al., "Nanolocomotion—Catalytic Nanomotors and Nanorotors," Small 6 (2), 159-167.). These have distinct drawbacks for biomedical applications or rheological applications in complex fluids and suspensions, as electric fields are difficult to apply in aqueous environments, optical forces require transparent media, and chemical reactions often require corrosive environments or special chemicals and are concentration-dependent.

One technique used to maneuver and control the motion of small scale objects in fluidic environments is the optical tweezer (A. Ashkin, J. M. Dziedzic, J. E. Bjorkholm et al., "Observation of a single-beam gradient force optical trap for dielectric particles," Opt. Lett. 11 (5), 288-290 (1986). David G. Grier, "A revolution in optical manipulation," Nature 424 (6950), 810-816 (2003)), where focused laser beams allow micron sized beads to be trapped and moved in solution. With recent technological developments, large number of beads could now be trapped and moved independently. While this technique has provided invaluable information in many biophysical problems, especially those involving rheological measurements, the optical traps are typically created very close to a microscope objective in an optically transparent sample, while requiring a powerful laser beam. This in turn excludes in-vivo applications, where either proximity to the biological sample or applying a strong laser beam is undesirable, or it excludes applications in complex fluids that are opaque and/or scatter laser light.

Methods, which reply on chemical reactions (R. Kline Timothy, F. Paxton Walter, E. Mallouk Thomas et al., "Catalytic Nanomotors: Remote-Controlled Autonomous Movement of Striped Metallic Nanorods13," Angewandte Chemie International Edition 44 (5), 744-746 (2005). Shakuntala Sundararajan, Paul E. Lammert, Andrew W. Zudans et al., "Catalytic Motors for Transport of Colloidal Cargo," Nano Letters 8 (5), 1271-1276 (2008). Jared Burdick, Rawiwan Laocharoensuk, Philip M. Wheat et al., "Synthetic Nanomotors in Microchannel Networks: Directional Microchip Motion and Controlled Manipulation of Cargo," Journal of the American Chemical Society 130 (26), 8164-8165 (2008).)), typically rely on some form on non-aqueous medium, such as hydrogen peroxide which severely limits their utility and excludes most in-vivo biological applications.

Electric fields have also been used to maneuver mm sized polymer gels and diodes (Y. Osada, H. Okuzaki, and H. Hori, "A polymer gel with electrically driven motility," Nature 355, 242-244 (1992). Suk Tai Chang, Vesselin N. Paunov, Dimiter N. Petsev et al., "Remotely powered self-propelling particles and micropumps based on miniature diodes," Nat Mater 6 (3), 235-240 (2007)); but these are only suitable for applications where electrodes can be placed in the sample.

Magnetic fields are less intrusive in most bio-environments and can be used in almost all complex fluids, including opaque and scattering media. Magnetic fields can act on diamagnetic, paramagnetic, and ferromagnetic structures and exert forces on these structures. The forces in turn can in principle be used to orient, align, and/or propel these structures. The detailed response of a structure depends on the magnetic properties of the structure, the nature of the applied magnetic field and the precise geometry of structure and the environment it is in. In the context of actuating and propelling magnetic structures in fluid environments—as described in this invention—paramagnetic, superparamagnetic and ferromagnetic structures interacting with magnetic fields are of importance.

A paramagnetic structure such as a bead can for instance be manipulated with a magnetic tweezer. Magnetic tweezers (F. H. C. Crick and A. F. W. Hughes, "The physical properties of cytoplasm: A study by means of the magnetic particle method Part I. Experimental," Experimental Cell Research 1 (1), 37-80 (1950).) rely on magnetic field gradients, and so it becomes necessary to arrange for a magnetic field whose strength varies with distance across the structure. This may be achieved with suitable gradient coils. The paramagnetic structure is 'pulled' by the magnetic field gradient in the direction of the stronger field lines. An asymmetric paramagnetic structure may also be aligned with a magnetic field.

Ferromagnetic structures can be aligned with a homogenous magnetic field as the magnetic field exerts a torque on a structure with a ferromagnetic moment. It is energetically favorable if the magnetic moment to be parallel to the magnetic field vector and this causes alignment of ferromagnetic moments with the field lines of a magnetic field. If the magnetic field rotates then a moment will follow the magnetic field. A structure that has a magnetic moment will therefore also start to rotate. This is used in the present invention to rotate a screw like object, which exhibits rotation-translation coupling, such that it propels forward (translates). The ferromagnetic structure experiences a torque that varies linearly with the strength of the applied magnetic field.

The advantages of using homogeneous vs. a gradient magnetic field for manipulating nanoparticles have also been considered (Jake J. Abbott, Marco Cosentino Lagomarsino, Li Zhang et al., "How Should Microrobots Swim?," The International Journal of Robotics Research, 0278364909341658 (2009)). It is also possible to use a combination (Choi Hyunchul and et al., "Two-dimensional actuation of a microrobot with a stationary two-pair coil system," Smart Materials and Structures 18 (5), 055007 (2009)) of homogeneous and gradient fields to move mm sized permanent magnets. Paramagnetic structures can be "pulled or pushed" with gradient fields.

In order to fabricate structures that respond to and can be manipulated and controlled with magnetic fields materials need to be used that possess suitable magnetic properties (i.e. paramagnetic, superparamagnetic or ferromagnetic) in addition to the structural properties that permit locomotion at low Reynolds numbers. One such structure is for instance a screw or screw-like or helical structure in conjunction with a ferromagnetic moment. Similar to a cork-screw or the flagellum of a bacterial cell, it is chiral, that is, it is handed, and can be propelled in low Reynolds number hydrodynamics by rotation. This invention describes the fabrication of structures that possess a ferromagnetic moment and that can be rotated with a magnetic field and that thereby can be screw-like propelled through solution, liquid, suspensions, tissue, or biological samples etc. by the application of suitable magnetic fields.

Henceforth, the description shall refer to "artificial swimmers", "artificial bacteria", "propellers", "micro-bots", "nano-bots" or in any structure that is larger than 20 nanometers in any of its dimensions and smaller than 100 microns in its dimensions and that can be propelled with magnetic fields and/or magnetic field gradients as Magnetically Actuated Propellers (MAPs). It is desirable that MAPs can be reproducibly made on a large scale by a fabrication method that is robust, and that can produce a large number of MAPs. Furthermore, for biomedical and rheological applications it is particularly important that the MAP structures can be propelled through solution or biological tissue or suspensions. The present invention describes the fabrication, actuation and propulsion of MAPs whose hydrodynamic properties are described by low Reynolds number hydrodynamics.

Existing methods for making artificial swimmers including MAPs have a number of shortcomings. 3D-lithographic techniques used to make structures that can be propelled from a distance are often limited to fabrication of MAPs on a few square millimeters. Also the ranges of shapes that can be made by these masking techniques are limited. Two-photon lithographic techniques can be used to make three-dimensional structures such as helices, which can in principle be used to realize MAPs, including systems described by this invention, but are time-consuming and in general do not permit the parallel fabrication of large numbers of MAPs. It is therefore more convenient to directly use vacuum deposition techniques that can give rise to structures, which can be used to make MAPs, which is also the preferred embodiment of the present invention.

For example, U.S. Pat. No. 6,304,768, describes a device and a method for using magnetic fields to move different types of magnetic delivery vehicles. Though it is to be noted that the described technique relies on positioning magnets for locating and guiding the magnetic vehicles, which may not work in an efficient manner with the MAPs and the examples of magnetic delivery vehicles as provided are completely different than what has been described in the present invention.

US Patent Application, published as US 2010/0242585 A1, teaches the method of using a device which is an object with no specific dimensions, for drilling mud. The structure of the proposed "nano-robot" is completely different from the MAPs which are the subject of present invention and the proposed applications are only limited to the measurement of mechanical properties of mud and gravel, and has no relation to biomedical applications.

A method for making structures in nanostructured thin films is described, for example, in U.S. Pat. No. 6,206,065, Robbie, K. J., et al. U.S. Pat. No. 6,206,065, however, said patent does not disclose the use of the vapor-deposited thin film for making structures that can be propelled from a distance in low Reynolds number fluids or soft matter including tissues and suspensions, and in particular it does not disclose use of the vapor-deposited thin film for making MAPs, and it does not disclose how to release structures from the substrate, and it does not disclose any rheological and biomedical applications.

While US Patent Application, published as US20110052393 A1, teaches a method of moving a magnetic device at low Reynolds numbers it is to be noted that the described device is different from the MAPs of the present invention, since the essence of the described device requires two interacting magnetic particles.

Further, US Patent Application, published as US 2010/0022857 A1, describes an intraocular sensor, part of which is magnetic. The described sensor geometry is different from the MAPs described in the present invention and is typically much larger than typical sizes in which the MAPs described in the present invention are fabricated. Also, the scope of the application is limited to intraocular measurements.

The US Patent Application, published as U.S. Pat. No. 7,220,310 B2, describes a system of nanobelts made of ZnO which are shaped like a propeller. The method of fabrication described is not as general or versatile as with MAPs of the present invention where various materials, sizes and geometries are easily obtainable, and U.S. Pat. No. 7,220,310 B2 fails to teach how the structure may be propelled (translated).

Crucial to the present invention is that the three-dimensional structure of the MAP permits the propulsion or actuation with a magnetic field such that the MAP can be controllably propelled. The present invention describes a system for fabricating large numbers of MAPs that is based on shadow growth vapor deposition. This invention described a propulsion method that uses magnetic fields in order to control and propel MAPs in solutions, suspensions, liquids, and tissue and other soft matter. Furthermore, the system and method of this invention permits large numbers of these structures to be fabricated simultaneously. Applications are described including but not limited to the diagnosis of diseases, delivery of drug molecules, and in the controlled delivery of MAPs and therefore materials and agents of therapeutic value.

A variety of magnetic materials can be used to accomplish the specific properties required to realize a MAP. For an object of volume, V, and magnetization per unit volume, $\vec{M}$, in a magnetic field flux density, $\vec{B}$, the applied torque, $\vec{T}$, and force, $\vec{F}$, are given by $\vec{T}=V\vec{M}\times\vec{B}$ and $\vec{F}=V(\vec{M}\cdot\vec{\Delta})\vec{B}$ respectively. While gradient fields can pull paramagnetic beads, the usage of homogeneous fields typically requires ferromagnetic character in the MAPs. It is important to consider material properties while designing a ferromagnetic MAP, since ferromagnetic structures show super-paramagnetic behavior, as they become smaller in size. The loss of ferromagnetism is essentially due to the absence of the motion of domain walls at small sizes, where the formation of domain walls becomes energetically unfavorable. Single domain particles are formed below some critical size and as the sizes are reduced further, the system becomes super-paramagnetic. The specific magnetic properties of materials are for instance listed under http://www.kayelaby.npl.co.uk/generalphysics/2_6/2_6_6.html and it is possible to find materials suitable for vacuum deposition and or electrochemical deposition that can be used in conjunction with Glancing Angle Deposition (GLAD).

SUMMARY OF THE INVENTION

In the first aspect, the present invention teaches a system and an associated method to prepare Magnetically Actuated Propellers (MAPs) and it also teaches their use for biomedical and rheological applications. The MAPs according to the present invention are screw like and are propelled by a magnetic field. Like a cork-screw that is rotated in order to drive it into a cork, the structures described in accordance with the present invention are rotated by a rotating force in a rotating magnetic field, that 'grabs' the magnetic moment of the MAPs and rotates the MAPs about their long axis. The rotation accordingly propels the MAPs through the medium of interest which includes but is not limited to a solution, fluid, or tissue it is located in. Systems for the fabrication of the MAPs as well as the methods to actuate and control the MAPs as well as applications that describe the usage of MAPs are described.

According to the second aspect of the invention the system for making magnetically actuated propellers (MAPs), capable of moving by means of magnetic fields, comprises a vacuum chamber holding a vapor source, a substrate holder holding a substrate onto which material from the vapor source is deposited, and a deposition-rate monitor for measuring vapor flux directed onto the substrate; and a process controller that controls a predetermined incidence angle theta formed by the direction of vapor flux and the surface normal of the substrate, as well as the direction of rotation and the rotation speed of the substrate about its axis during deposition, wherein the process controller is configured to receive measurements from the deposition-rate monitor and to monitor those measurements and to generate and communicate commands to adjust the rotation speed and tilt angle of the substrate holder in response to the measured vapor flux, wherein the vapor flux can be adjusted and wherein the source of vapor can be changed without breaking vacuum.

The process controller is configured to generate commands to vary the tilt angle and the rotation speed during deposition so as to promote growth of structures of predetermined shape, and in particular, surface morphologies that permit their propulsion through fluids, solutions, tissue, biological matter, complex fluids, suspensions and mixtures by means of a magnetic field.

The process controller is adapted to rotate the substrate at rotation speeds that promote the growth of helices or screw-like structures.

The MAPs are fabricated using a shadow masking technique, known as "glancing angle deposition", and are made to contain a ferromagnetic material. Magnetization of the MAPs makes the MAPs ferromagnetic with a moment that is preferably along the short axis of the screw. The fabrication method can be used to reproducibly make large numbers of MAPs where the size and precise shape of the MAPs can be optimized so as to obtain the best control and motion for a particular medium.

According to another aspect, the present invention provides a method for making Magnetically Actuated Propellers (MAPs) comprising providing a vapor source, a substrate and a vapor source; rotating the substrate about an axis normal to the substrate surface; directing vapor flux from the vapor source at a surface of the substrate to deposit material on the substrate surface with the substrate surface positioned at a non-zero angle theta with respect to the direction from which the vapor flux is directed at the substrate; monitoring the flux rate with a deposition-rate monitor; and controlling deposition rate, rotation rate, and surface angle with a controller.

Further, different vapor sources are provided to deposit a different material on the substrate surface. The method further comprises depositing a magnetic material and/or depositing a magnetic material on a first deposited material, where the deposition of the first material results in a surface of a shape, and morphology for allowing propulsion by a rotation about the structures long axis, and ferromagnetic moment in the magnetic material deposited thereon. According to the invention the substrate is made of glass, silicon, a metal, a salt, an organic medium, or even plastics. The materials are deposited simultaneously or sequentially. One or more of the deposited materials can include a material that promotes adhesion, such as chromium, titanium etc.

The method further comprises patterning the substrate by depositing nanoparticles or microparticles onto the surface prior to depositing the vapor, wherein the particles have a size between 10 nm and 10000 nm. The substrate can also be patterned by colloidal or nanoindent or nanoimprint lithography or any other suitable lithography such that the patterned substrate grows regular MAPs at the patterned positions.

The rotation rate and tilt angle are governed to promote the growth of structures, such as helices, or propeller- or screw-like structures.

An embodiment of the method includes vacuum deposition using a shadow-growth method, such as oblique-angle deposition with motor-controlled rotation of the substrate (as described in U.S. Pat. No. 6,206,065 and U.S. Pat. No. 5,866, 204). The material that permits the formation of structured including screw- or propeller-like structures in large numbers onto a planar or a nonplanar substrate, which can also include particulates or seed particles and that material, may in turn be magnetic.

The propeller structures can be removed from the substrate in a variety of ways. Simply sonicating or vibrating the substrate may release the propellers. Also, a release layer can be added to the substrate prior to depositing the propellers. By etching the release layer (e.g. in one embodiment a release layer of NaCl can be dissolved by water after vacuum deposition), the propellers can be freed from the substrate.

If not already included in the initial vacuum deposition step, then the magnetic material can be deposited in a subsequent step, which may or may not be based on physical vapor deposition. The deposition of the magnetic layer is either under normal incidence or some other angle of incidence including an oblique angle of incidence. The magnetic layer can also be deposited under motor control of the substrate, including substrate rotation. In addition, controlling (and lowering) the temperature of the substrate during deposition can be advantageous. For example, with certain materials, cooling the substrate (e.g. to liquid-nitrogen temperatures or lower) during evaporation reduces the surface mobility of the evaporated material.

The MAPs can be functionalized and suitable molecules can be bound onto their surfaces if these surfaces can be chemically modified. The MAPs may also be made from materials that in themselves carry a function or are of use in biomedical and/or diagnostic and/or therapeutic applications. Rheological function in complex fluids for mixing, dispersion or sensing purposes can be accomplished with the structures. The structures can also be used to enter biological tissue, and/or organs, and/or to enter cells, and perform complex functions such as delivering DNA, drug molecules, chemicals, nanoparticles, genetically modified materials, viruses or other bio-active substances etc at a desired location, including specified intra- or extra-cellular regions.

The present invention is also capable of other and different embodiments, and its several details can be modified in various obvious respects, all without departing from the scope of the present invention. Accordingly, the drawings and descriptions are to be regarded as illustrative in nature, and not as restrictive.

DETAILED DESCRIPTION OF THE INVENTION

The foregoing and other features and advantages of various aspects of the invention will be apparent from the following, more-particular description of specific embodiments. These specific embodiments are offered herein for the purpose of exemplification within the broader bounds of the invention.

Figure 1:
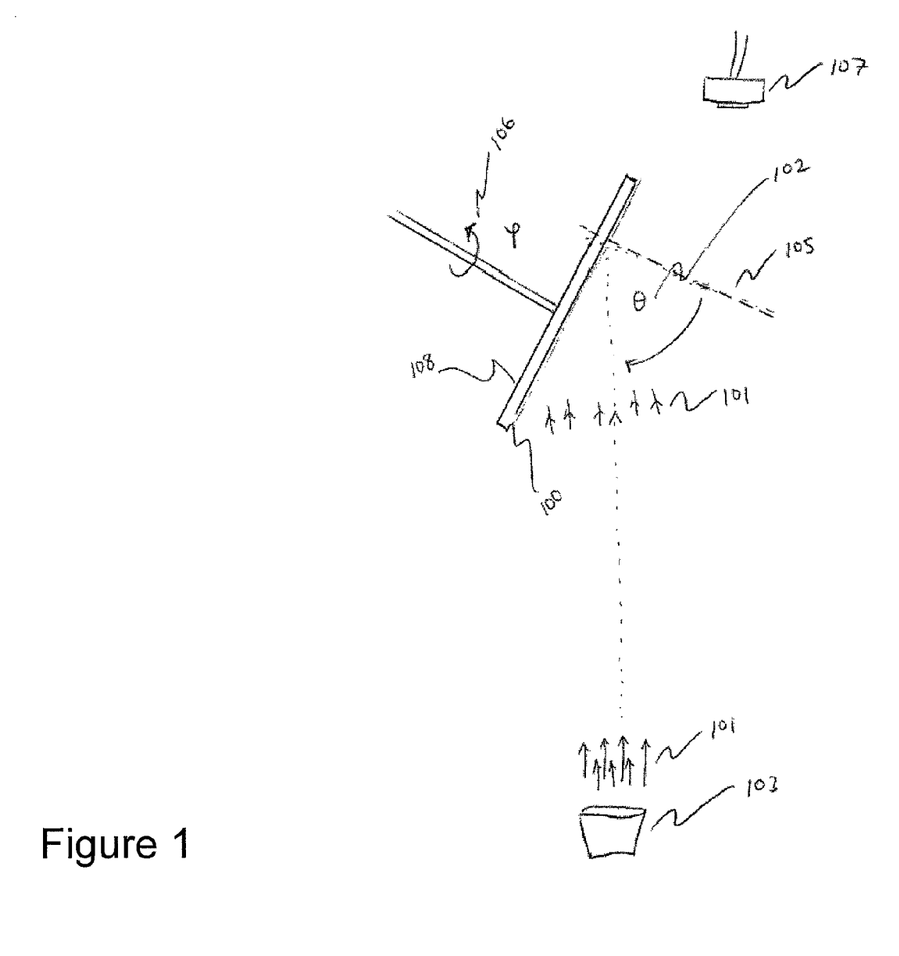
FIG. 1 shows a schematic of an oblique incidence evaporation setup.

FIG. 1 depicts schematically the system used to make nanostructured surfaces which form the basis of MAPs. Not shown is the vacuum chamber in which the setup typically resides and which provides pressures of $<10^{-4}$ Torr. Structured surfaces may be deposited when the substrate 100 is tilted with respect to the flux of the material 101 that is to be deposited, due to shadow masking. The substrate 100 may be a clean and flat surface, such as a Si or glass wafer, or it may already exhibit some surface structure. In addition it is possible to lithographically pattern or it is possible to deposit particles or similar material to enhance the structure present on the surface. Deposition, e.g. via electron-beam (e-beam) deposition from a crucible 103, of some suitable material will then give rise to a surface that exhibits nanostructure, such as a helical shape. The precise geometry of the screw-like objects may vary. The sense of the helicity can vary, but the helicity is important for propulsion. The angle of incidence θ 102 of the material flux direction 101 with respect to the surface normal 105 is typically >80°. Preferably the predetermined incidence angle theta of the vapor flux is high, e.g. greater than 65 degree. In addition motor control is provided such that the substrate 100 can be rotated about its own axis, the rotation angle φ 106, at varying speeds. It is advantageous if the tilt angle θ 102 can be changed during deposition. Further, the system typically has a deposition rate monitor 107 which gives a measure of the material flux at the substrate. Apparatus for providing the specified rotation and tilt is described in K. Robbie, G. Beydaghyan, T. Brown, C. Dean, J. Adams, C. Buzea, "Ultrahigh vacuum glancing angle deposition system for thin films with controlled three-dimensional nanoscale structure", Review of Scientific Instruments, vol. 75, (2004), 1089. A commercial sample stage that can be used to manipulate the substrate in a GLAD process is also available from Pascal Technologies, as described at http://www.pascaltechnologies.com/Products/ProductDetails.cfm?SubCategoryID=838. Aspects of the surface roughness that can be obtained with GLAD are described in B. Dick, M. J. Brett, T. Smy, "Investigation of substrate rotation at glancing angle incidence on thin-film morphology", J. Vac. Sci. Technol. B 21, (2003), 2569.

Computer control is used to adjust the rotation speed of the substrate, and possibly the timing and rate at which the rotation or tilt is adjusted, according to the measured deposition flux. Alternately computer control is used to maintain a constant deposition rate while the substrate is rotated at a predetermined rotation speed. The computer can be a personal computer including a processor coupled with a computer-readable medium storing software for controlling the process; the computer can also include input and output ports (e.g., USB ports) for receiving measurements from, e.g., a deposition-rate monitor (which measurements are utilized by the processor per instructions in the software code to regulate the process) and for communicating commands generated by the processor to control the components [e.g., to the motor(s) that rotate and tilt the substrate]. A provision for cooling the substrate (e.g., a conduit through which liquid coolant flows) can be mounted on the back side of the sample holder 108.

Figure 2:
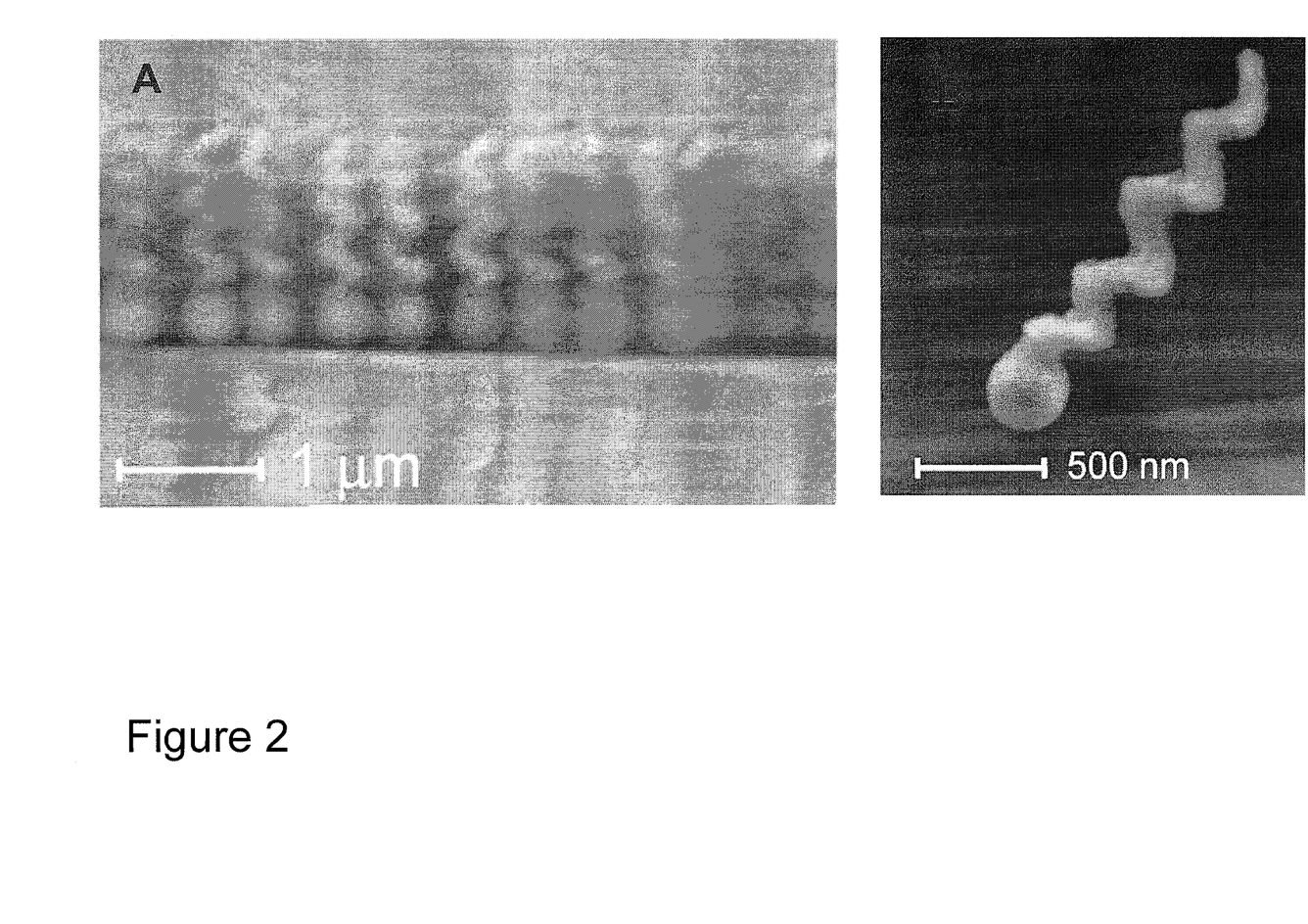
FIG. 2 shows (A) examples of a surface made of helical nano-structures that can be fabricated from an oblique incidence evaporation setup. (B) a sub-micron screw shaped nano-structure made from silicon dioxide prior to its magnetization of the MAP.

FIG. 2(A) depicts a surface made of helical nano-structures that can be fabricated from an oblique incidence evaporation setup. By controlling the rotation and tilt of the substrate stage during oblique angle deposition, while measuring or controlling the rate of evaporation, such a surface can be fabricated. (B) Individual screw-shaped nanostructures (nano-propellers) can be obtained by releasing the individual screw shaped nanostructures from the nano-structured surface. The shaped nanostructures can be made in a variety of materials and sizes and exemplify a particular embodiment of the MAPs described in this invention.

Figure 3:
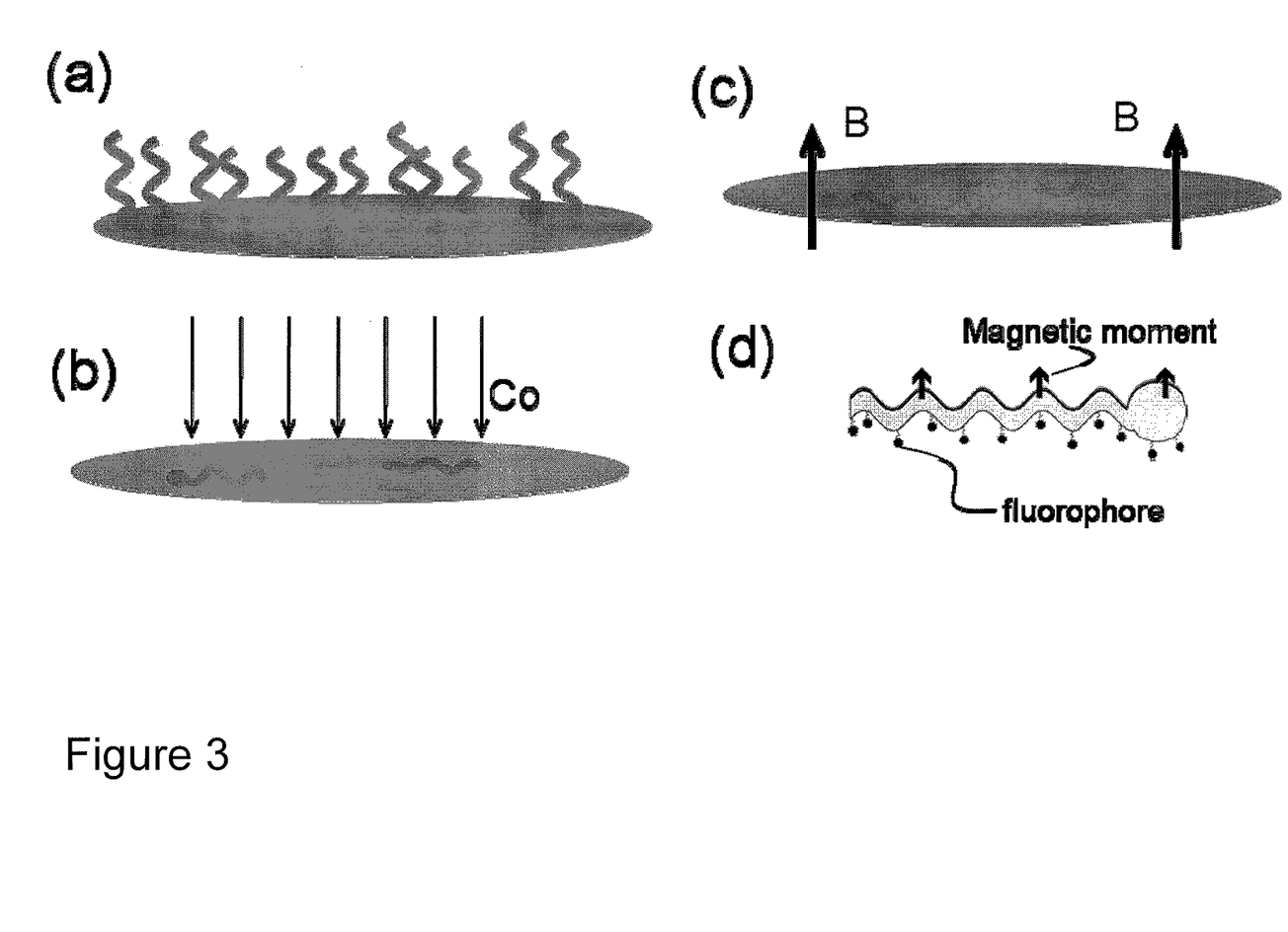
FIG. 3 shows one possible fabrication method of making nano-structured propellers (one embodiment of MAPs), (a) Nano-structured thin films (b) Making individual magnetic nano-propellers (c) Magnetizing the propellers (d) Schematic of the magnetic nano-structured propeller.

FIG. 3(A) depicts one possible fabrication method of making MAPs. (a) Nano-structured thin film of helices or screw-like structures can be made by oblique angle deposition, such as GLAD. (b) the individual propellers are released from the substrate and laid on a second substrate, on which a ferromagnetic material, such as Cobalt (Co) is evaporated or sputtered or chemically deposited onto the structures. Similarly other materials can be sputtered or evaporated, possibly in addition to the ferromagnetic material (Cobalt in this particular example) to confer desirable thermal, electrical, magnetic, optical, chemical, and/or biochemical properties to the structures. (c) The propellers are magnetized such that their permanent magnetic moments are perpendicular to their long axis, and thereby the MAPs carry a permanent magnetic moment that is orthogonal to the long axis of the MAPs (d) Schematic of a MAP where chemicals (here, fluorescent molecules shown) are attached (chemically bound) to the propeller. Other molecules including biological- and drug-molecules may also be coupled to the MAPs. The schematic depicts a particular fabrication method and the various steps may for instance be extended by including additional or different fabrication steps (or the fabrication may be changed by leaving out a number of the steps schematically depicted). For instance an example of a different fabrication methodology of the MAPs may for instance replace the evaporation of magnetic material with electrochemical growth the magnetic material.

Figure 4:
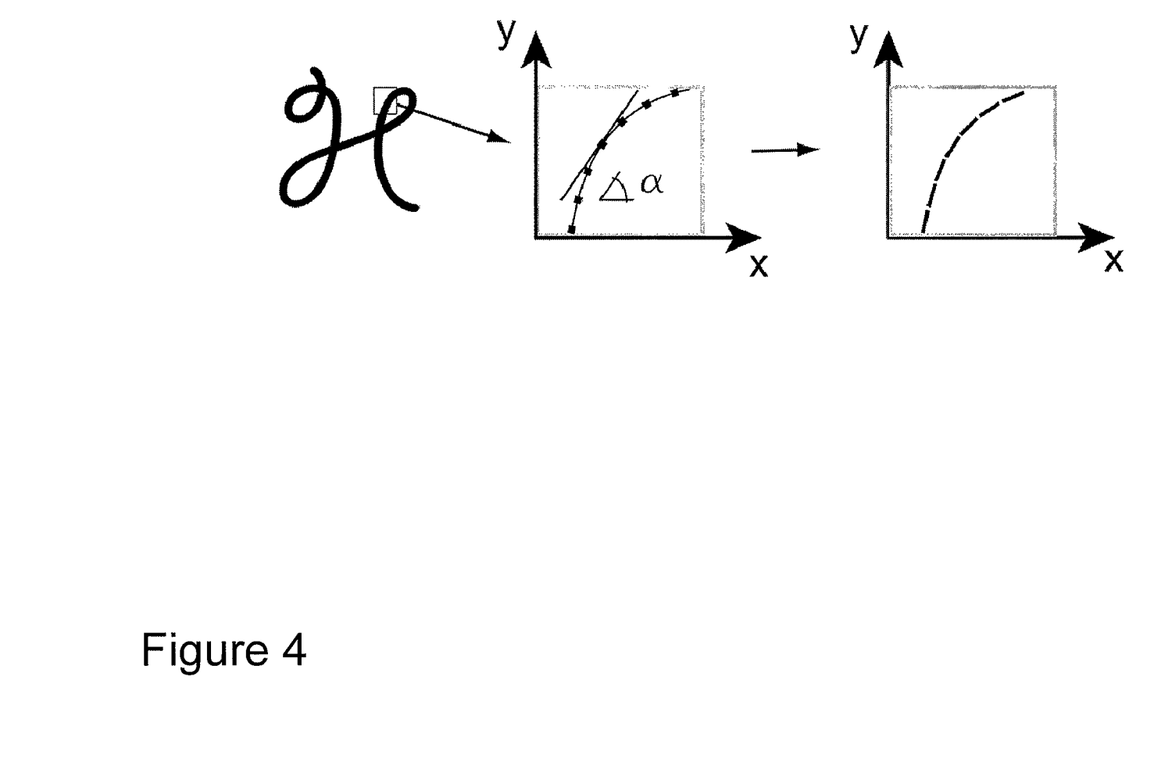
FIG. 4 shows the principle of controlling the motion of the nano-structured propellers along some particular trajectory.

FIG. 4 shows the principle of controlling the motion of the MAPs along some particular trajectory. The magnetic moment of each propeller in solution will align in the presence of the coils' magnetic field. By changing the direction of the field from the Helmholtz-coils the propellers are moved through solution, as we describe below. Linear propulsion along the y direction is for instance achieved by a magnetic field that rotates in the x, z-plane. The magnetic moment of the propeller follows the magnetic B-field. By virtue of the difference of the propellers drag coefficients it will orient such that it rotates about its long axis. This results in motion along the y-axis. The chirality of the propeller together with the rotation sense of the field ensures that each propeller will move along a defined direction (i.e. depending on its handedness either along +y or −y). In the particular example depicted in the figure, motion along letter "H" is shown. Letter "H" is divided into segments of equal length. The tangent in the x, y plane is computed for each segment to obtain linear segments of equal length. These correspond to the direction the MAP is moved along. A change of direction occurs after each segment. In order to move the propeller along the linear segment (direction of tangent), the x, y, and z coils are driven to give appropriate time varying magnetic fields.

Figure 5:
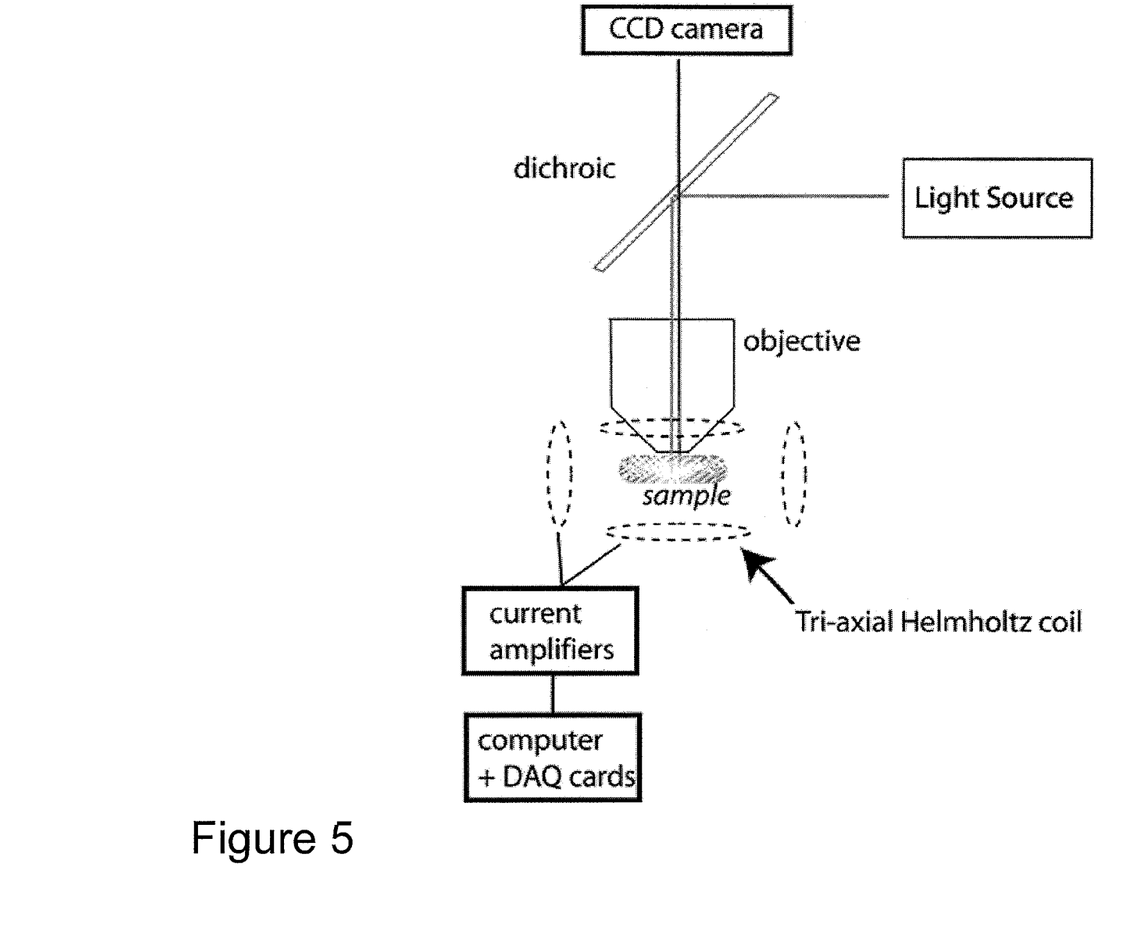
FIG. 5 shows a schematic for controlling the motion of the nano-propellers (MAPs) while visualizing them in a microscope.

FIG. 5 depicts a schematic for controlling the motion of the MAPs, while visualizing them in an optical microscope. The sample containing the propellers is kept around the focal plane of a microscope objective. The fluorescent microscope is depicted by a light source, dichroic and the objective. The CCD camera can be used for imaging the sample including the propellers. The propellers are moved by externally applied magnetic fields in 3 dimensions, created by a tri-axial Helmholtz coil. The current to the Helmholtz coil can be obtained from current amplifiers, which in turn can be controlled by a computer and data acquisition cards.

Figure 6:
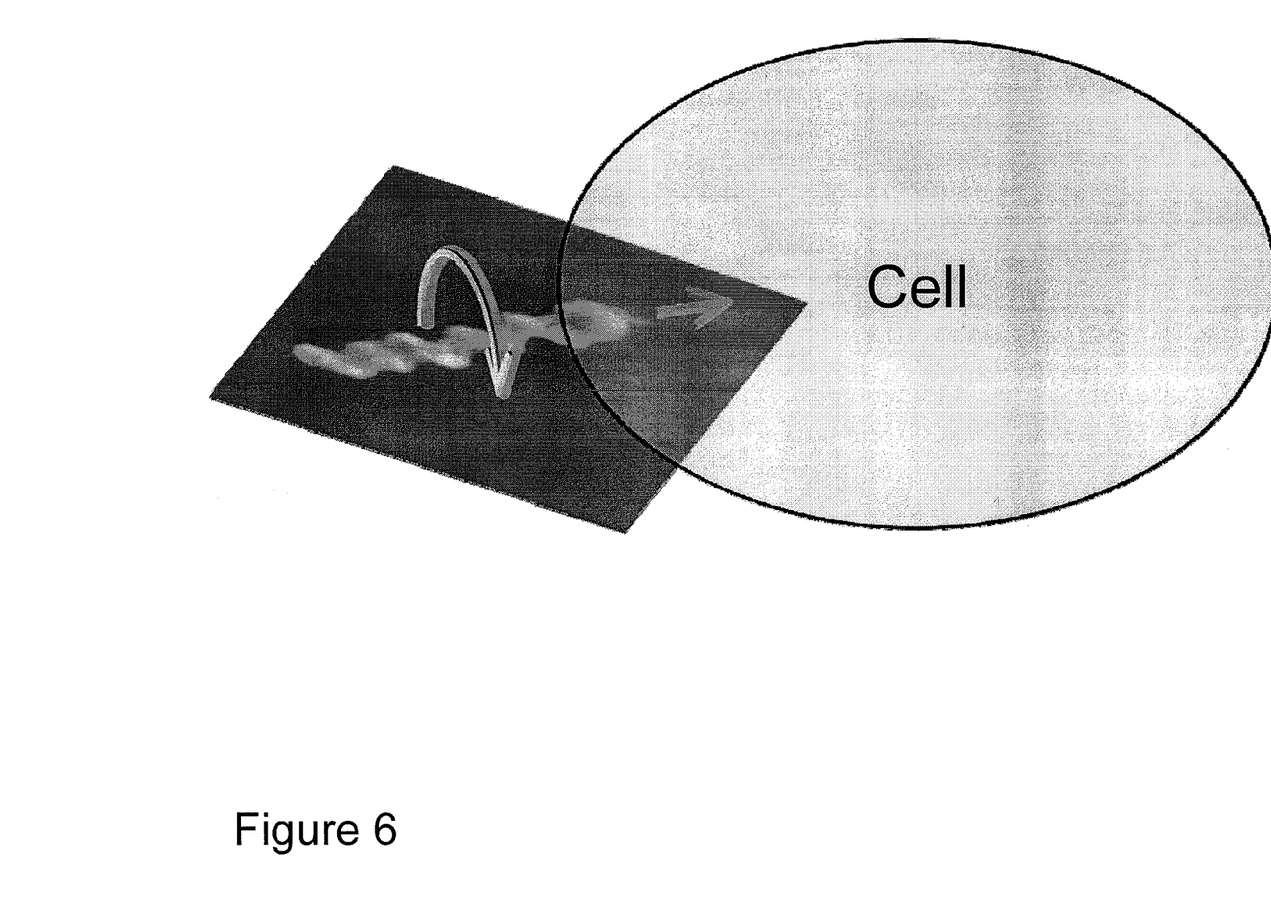
FIG. 6 shows a schematic for moving a MAP to enter a cell

FIG. 6 depicts a schematic for moving the nanopropellers to enter a cell. Chemical loads, e.g. DNA or drug molecules or other molecules or particles can be attached to the MAPs. The nano-propellers may be able to enter cells through direct puncture, e.g. like a screw drilling into a wall, or in another possibility, the bio-conjugated propellers may be internalized by the cells through phagocytosis or some other method of cytosis.

Figure 7:
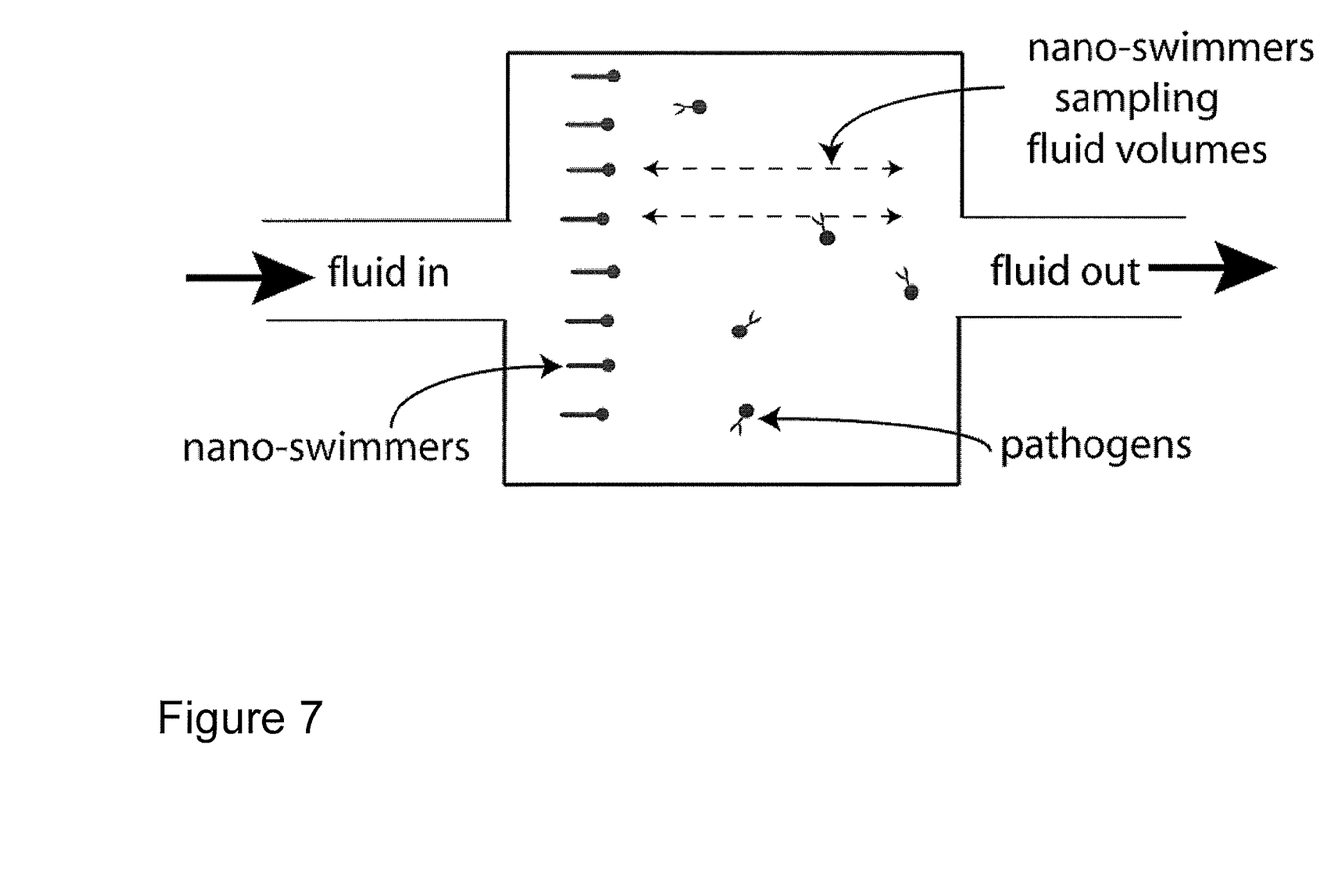
FIG. 7 shows a schematic of a microfluidic device suitable for biosensing applications using MAPs

FIG. 7 shows a microfluidic device where the MAPs can be used as a part of a bio-sensing system. The fluid inlet and outlet are shown through which a fluid containing certain bio-molecules or other molecules will enter and exit the microfluidic device. The hydrodynamic and chemical properties of the MAPs are modified when the target molecules bind and/or adhere to the MAPs. The nanostructured propellers will be actively moved to sample the fluid volume in order to increase the likelihood that a target molecule is captured (bound or adheres) by the MAPs.

Figure 8:
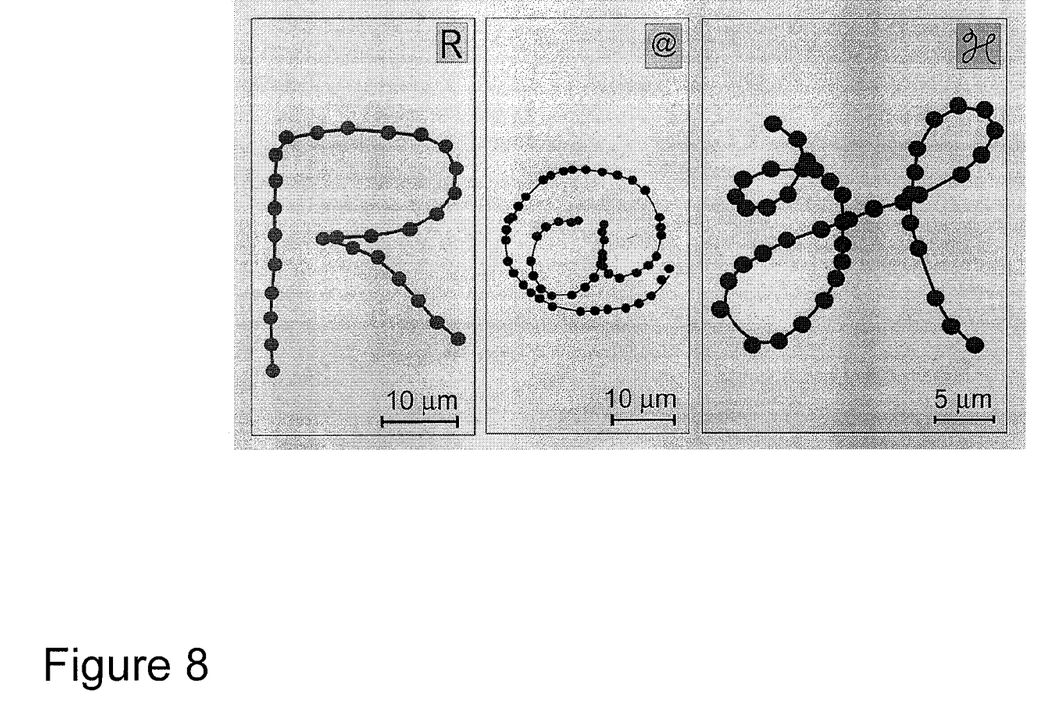
FIG. 8 shows the level of control achievable in the motion of a particular embodiment of a MAP, here a nano-structured propeller.

FIG. 8 shows the level of control achievable in the motion of a particular embodiment of a MAP in water that has been fabricated using the GLAD process. In this example, a micron sized nano-structured propeller has been used to trace out pre-programmed trajectories in a microfluidic device. The trajectories traced out are "R", "@" and "H". Micron level control can be achieved.

Figure 9:
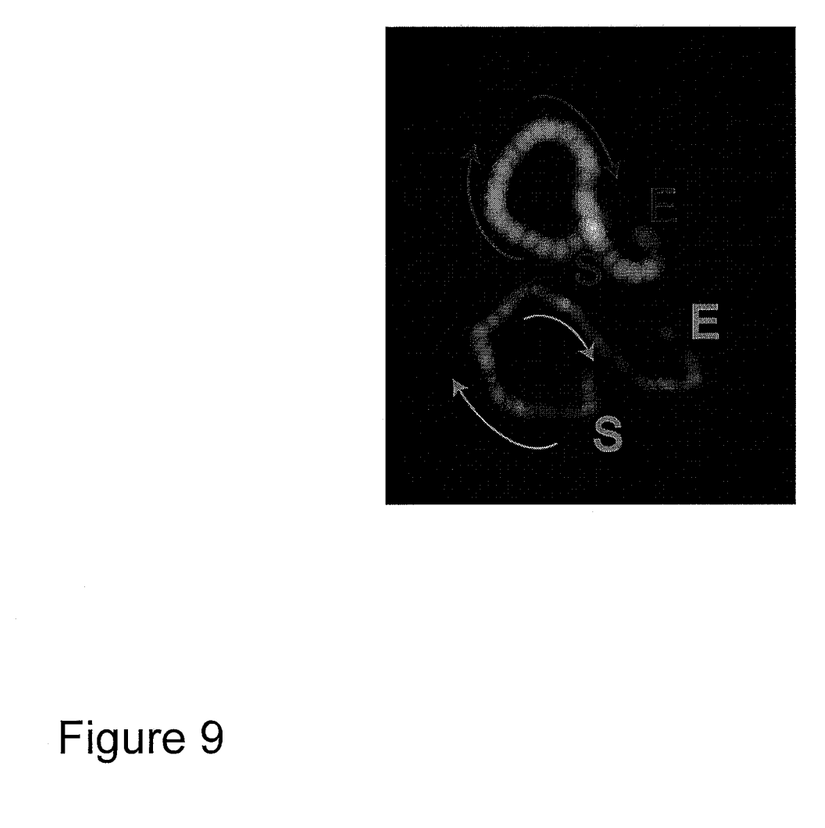
FIG. 9 shows the compound image of two MAPs, where the two swimmers follow similar trajectories in water.

FIG. 9 shows the compound image of two MAP structures follow similar paths under the action of a magnetic field pre-programmed to follow a curved trajectory from start (S) to end (E). A large number of identical propellers are expected to move along similar trajectories.

Figure 10:
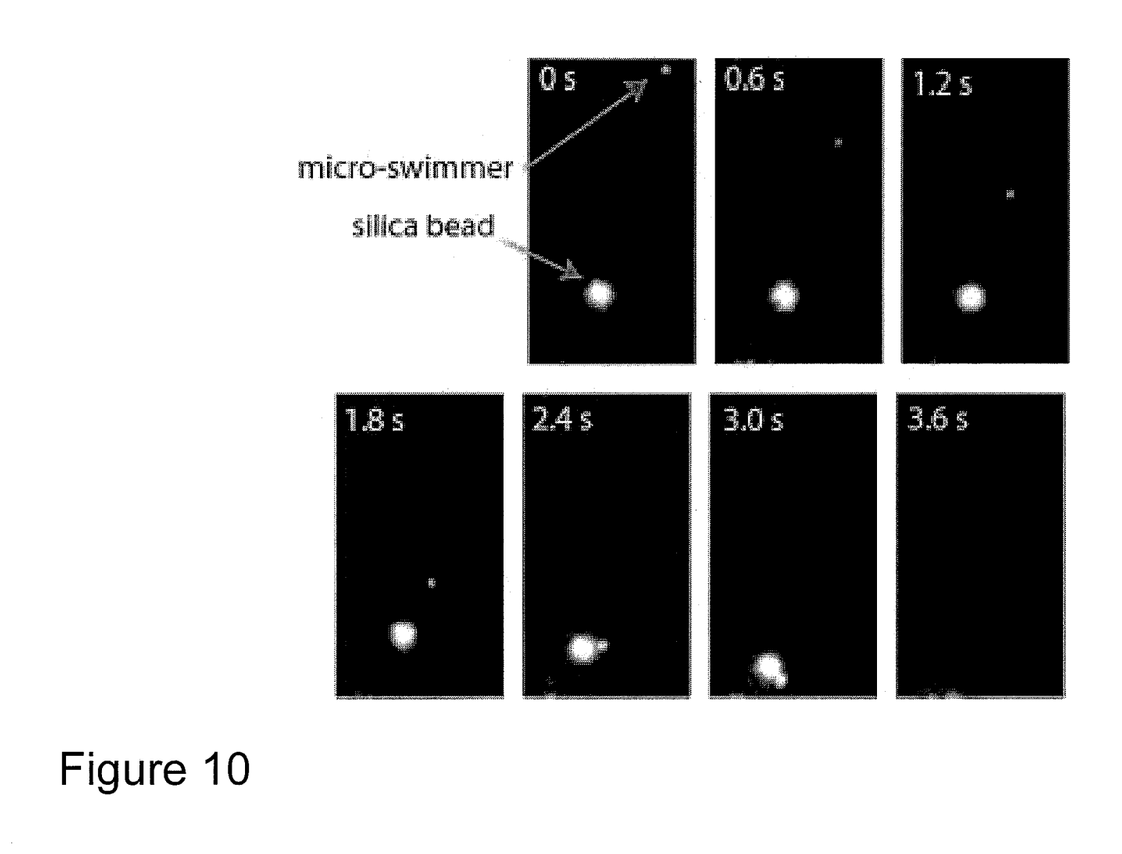
FIG. 10 shows how a nano-structured propeller can be used to push a load

FIG. 10 shows how a MAP (nano-structured propeller) can be used to push a load. A silica bead (5 micron diameter) is being pushed by a nano-structured propeller (1.5 micron long, 200 nm wide). The images (from left to right) show how the propeller approaches the bead and pushes it out of the field of view. A 40× microscope objective was used, and, the time gap between consecutive images is about 0.6 seconds.

According to the present invention MAPs are fabricated via an evaporation scheme for instance by directly evaporating a magnetic material. Subsequently one or a multitude of materials, which may be magnetic or non-magnetic, can be added via a different method, including but not limited to surface functionalization methods, chemical vapor deposition, physical vapor deposition, electrochemical methods etc. Further, it is also possible to first fabricate non-magnetic propellers via an evaporation scheme and subsequently a magnetic material is added via a different method, including but not limited to surface functionalization methods, chemical vapor deposition, physical vapor deposition, electrochemical methods etc. Yet another scheme may be used to fabricate the MAPs using a lithographic scheme and/or electrochemical method and/or polymerization scheme and/or physical and/or chemical vapor deposition.

The magnetic propellers of the present invention are magnetic propellers are magnetically actuated in a suitable environment, including but not limited to biological tissue, aqueous suspensions, complex fluids, organs, cells and cell cultures. The magnetic actuation of the magnetic propellers is done by the application of magnetic field that in addition may or may not contain a gradient and that may or may not vary in time. The said magnetic field be a homogenous magnetic field or a gradient magnetic field or a combination thereof. Rotating homogenous magnetic fields of suitable frequencies can be used to rotate the magnetic propellers containing ferromagnetic moments, such that the magnetic moments of the propellers experience a torque and the MAPs are rotated by the rotating magnetic fields.

When the magnetic fields used to actuate the magnetic propellers are generated by passing current through current carrying coils, including but not limited to Helmholtz and Maxwell coils, the currents used to drive the current carrying coils are typically generated by an electronic instrument such as a multitude of current amplifiers. When the currents used to drive the current carrying coils or the electronic instrument used to generate the currents are controlled by an electronic instrument, or a computer controlled instrument, such as a data acquisition card. Alternately, the magnetic fields used to actuate the magnetic propellers can for instance be generated by manipulating permanent magnets.

The magnetically actuated propellers may also be used for rheological measurements and applications thereof. If the MAPs are not magnetically actuated and simply placed in a suitable measurement; then observation of their thermal (Brownian) motion can be observed and/or imaged in a suitable device. This (passive) motion of the MAPs can then be used to measure and infer rheological properties of the surrounding environment, such as the viscosity, elasticity etc.

The propellers may also be magnetically actuated to probe the mechanical and/or viscoelastic and/or rheological properties of the surrounding medium. The magnetically actuated propellers can be propelled (active motion) in a suitable environment to push and deform an object, such as but not limited to a biological membrane, and thereby perform rheological measurements by imaging the deformation of the membrane as a function of the applied thrust originating from the magnetically actuated propellers. The magnetically actuated propellers can also be propelled in a suitable environment, such as but not limited to a biological tissue or fluid and thereby measure the rheological properties of said medium The rheological properties may also be determined by a combination of active and passive motion of the MAPs.

The magnetic propellers are used for sensing purposes, such as but not limited to bio-molecules, bio-pathogens and chemicals. The propellers are placed in an environment containing target objects, such as but not limited to bio-molecules, bio-pathogens (virus, bacteria etc. and chemicals. The propellers are magnetically actuated to travel across a sample volume and thereby increase the probability of binding the target molecules or objects.

The MAPs may also be placed and/or actuated in a medium containing target molecules or objects, and upon conjugation with the target molecules and/or objects the rheological properties or other properties of the MAPs, such as their optical and/or hydrodynamic and/or chemical properties are modified which in turn is a measure for the binding of the MAPs to said target molecules and/or objects. A multiplexed sensing system may be realized where a number of different targets may be detected by said means. In case where the MAPs are conjugated to certain chemicals, including but not limited to DNA, drug- or therapeutic-molecules or particles and subsequently used for delivering said chemicals, in a suitable environment, such as but not limited to specific tissue, organs, cells, or cell cultures etc. One or many conjugated MAPs are propelled in a tissue or an organ to deliver certain chemicals, particles, and/or materials, e.g. drug molecules in a specific region of a body, e.g. a particular tissue and/or organ and/or membrane.

Examples

Example 1

In one embodiment seed particles, such as spherical silica particles or polystyrene particles of a suitable diameter (e.g., between 10 nanometers and 10 microns), are deposited onto a suitable substrate, such as a wafer formed of silicon or silica. In one embodiment, the seed particles form a monolayer on the surface. A uniform layer of seed particles can be achieved by depositing the particles (in an amount that will cover the surface with a close-packed monolayer) in a solution onto the surface of the substrate and by letting the solvent evaporate. The substrate is at a regulated (cooled) temperature and is isolated from vibrations and air flow. Cooling reduces surface diffusion of the deposited material. Alternately, a fluid containing seed particles is spin-coated onto the substrate.

Alternately, the seed particles are deposited onto a surface and subsequently transferred onto the substrate using a Langmuir Blodgett trough.

Chemicals can be used to facilitate the adhesion of the seed layer. As seen in FIG. 2A, seed particles can form a uniform layer on the wafer; and when the substrate is used in a glancing angle deposition, these seed particles promote the growth of regular surface structures, such as helices made of silicon dioxide (see FIG. 2). In one embodiment, the substrate coated with seed particles is placed in an evaporation system where the vapor flux of a suitable metal, magnetic material (material that can be magnetized), or oxide such as silicon dioxide is incident onto the substrate containing the seed particles at an oblique angle theta>70 degree. FIG. 1 depicts schematically the system used for the glancing angle growth of structures that form MAPs.

FIG. 3 shows schematically how the helices stand on the wafer (FIG. 3A) and how these are subsequently removed, a magnetic material is evaporated, which in one embodiment can be cobalt of a thickness of 20 nm, how the structures are magnetized in an electromagnet, such as a Walker 7HV capable of generating fields of >10000 Gauss, and finally their surface is chemically functionalized, which in one embodiment can be achieved by coupling fluorophores such as Rhodamine 6G via amino-silane coupling chemistry.

Example 2

A preferred embodiment is described in the publication by Ambarish Ghosh and Peer Fischer, "Controlled Propulsion of Artificial Magnetic Nanostructured Propellers," Nano Letters 9 (6), 2243-2245 (2009).

Example 3

In one embodiment the seed particles are replaced by suitable patterns formed by a lithographic technique, such as, but not limited to, nanoindent or colloidal lithography or nanoimprint lithography. Similarly other techniques such as deep UV lithography, phase shifting lithography, electron beam lithography, photolithography etc. can be used as well. The patterns are locations that initiate the shadow growth. By adjusting the height, shape and size as well as the spacing between these seed patterns it is possible to grow regular shapes using shadow-growth methods such as GLAD and to affect the size and shape of the shadow-grown structures.

Example 4

In one embodiment during the evaporation of the oxide, such as silicon dioxide, or magnetic material, such as cobalt, the substrate can be rotated about its normal at a rate that allows helical structures to be grown. A quartz crystal constantly measures the vapor flux during deposition and a controller adjusts the tilt angle and the rotation speed of the substrate.

Example 5

In another embodiment, a material that is not magnetic is co-deposited with a material that is magnetic. The substrate is a silicon wafer or a glass wafer. The vapor flux is incident onto the substrate at an oblique angle theta greater than 70 degree (e.g., 87 degree). During the evaporation and deposition of the silicon dioxide, the substrate is rotated about its normal at a rate between about 0.01 and 100 rpm (including at a rate of about 1 rpm), though the rate of rotation can vary along with the rate of vapor flux. A quartz crystal constantly measures the vapor flux and a controller adjusts the rotation speed of the substrate. The angle of incidence of the flux (theta), the rotation speed of the substrate, the temperature of the substrate, and the amount of silicon dioxide that is deposited are subject to control; and all determine the final morphology and the form of the structure. In addition, seeding the substrate, as described in example 1, can be used to affect the shape and form of the deposited structures. The tilt angle, theta, of the substrate determines the amount of shadowing during deposition and, therefore, directly influences the diameter of the MAPs. After deposition of the non-metal, deposition of chromium or a titanium layer on the non-metal before depositing the magnetic material can be advantageous.

Example 6

In yet another embodiment, the material that has been vapor deposited at a glancing angle is subjected to an etching procedure. One such method is to use wet etching or a suitable chemical or ion etching. After cleaning, the substrate is returned to the vacuum chamber; and additional layers are deposited. This is closely related to the many ways in which the propeller structures can be removed from the substrate. Simply sonicating or vibrating the substrate may release the propellers. Also, a sacrificial release layer can be added to the substrate prior to depositing the propellers. By etching the release layer (e.g. in one embodiment a release layer of salt (e.g. NaCl) can be dissolved by water), the propellers can be freed from the substrate.

Example 7

In yet another embodiment, a more-complex surface morphology is used; for example, the structures. The range of the structures of the film can also include zig-zag patterns, columnar structures, pillars, screws, helices that are handed, as well as combinations of these patterns; e.g., a surface can contain pillars that have a certain length followed by a helical morphology, ribbons or helices that have one handedness; and then during growth, another columnar structure is added, and the surface then consists of structures that are helical with one handedness for some length away from the wafer onto which they were deposited followed by a length where there is no handedness etc.

Other materials can readily be substituted for the materials mentioned in the examples. The magnetic and chemical properties of the materials will influence the nature of the applications and properties of the MAPs. Similarly, more-complex layered structures can be grown by these methods, in particular those that contain more than one evaporated material and/or metal and or magnetic material. Further, the surfaces can, in addition, be modified by chemical methods, such as those that facilitate the binding of molecules, in particular those that have biological significance, such as drug molecules, nanoparticles, antibodies, etc. or can be made to be porous. One can, for instance, also readily couple functionalized thiols or silanes in order to anchor molecules to a suitable surface.

Example 8

In visualizing and tracking the MAPs a fluorophore in conjunction with optical illumination and microscopy may be used as is described in the publication by Ambarish Ghosh and Peer Fischer, "Controlled Propulsion of Artificial Magnetic Nanostructured Propellers," Nano Letters 9 (6), 2243-2245 (2009). However, in yet another embodiment the MAPs may be tracked by virtue of their magnetic properties, e.g. they may be imaged using Magnetic Resonance Imaging (MRI). The coils of the MRI setup may in addition be used to manipulate and steer the MAPs. In yet another embodiment the MAPs may be imaged by ultrasound, X-rays, optical means, or combinations thereof.

Example 9

In yet another embodiment the magnetic field used to steer the MAPs is provided by a three-axis Helmholtz coil as is described in the publication by Ambarish Ghosh and Peer Fischer, "Controlled Propulsion of Artificial Magnetic Nanostructured Propellers," Nano Letters 9 (6), 2243-2245 (2009). Other coil geometries and formations may be used. For instance a Halbach magnet can be used instead of the coils.

Example 10

In yet another embodiment the magnetic material is deposited onto a GLAD structure by electrochemical means. A suitable material for electrochemical deposition that can be ferromagnetic is for instance Nickel.

Example 11

In yet another embodiment the MAPs are made using a shadow growth method using entirely ferromagnetic materials such as cobalt.

Example 12

In yet another embodiment the MAPs are driven into biological tissue or an organ. Or they are propelled under observation in a microscope to enter a cell or several cells. It is possible that biologically active material has been anchored onto the surface of the MAPs, or their material composition is such that it serves a purpose in itself. The materials may therefore exhibit a number of physical, chemical, optical, thermal, cytotoxic, etc. functions.

Example 13

In yet another embodiment a paramagnetic bead is used as a seed particle, or a paramagnetic material is deposited in addition to a ferromagnetic material.

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by ½0th, ⅟10th, ⅕th, ⅓rd, V2, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents, patent applications and articles, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed is:

1. A method for making magnetically actuated propellers (MAPs) configured to be moved by magnetic fields, the method comprising:
   providing a vapor source and a substrate in a vacuum chamber;
   rotating the substrate about an axis normal to a surface of the substrate at a rotation rate;
   directing a vapor flux having a flux rate from the vapor source in a direction toward the surface of the substrate to deposit at least one material on the surface of the substrate, with the surface of the substrate being positioned at an angle theta that is different from zero with respect to the direction from which the vapor flux is directed toward the substrate;
   monitoring the flux rate with a deposition-rate monitor to establish a deposition rate;
   controlling the deposition rate, the rotation rate, and the angle with a controller;
   governing the rotation rate and the angle to promote the growth of structures comprising at least one of a chiral structure, a helical structure, a propeller-like structure, and a screw-like structure; and
   releasing the structures from the substrate using a method comprising at least one of sonication, vibration, agitation, dissolution, and etching.

2. The method of claim 1, further comprising:
   providing at least one further vapor source to deposit at least one different material on the surface of the substrate, the at least one different material being selected from the group consisting of: silicon, glass, and plastic materials.

3. The method of claim 1, further comprising:
   patterning the substrate by a method comprising at least one of lithography, nanoimprint lithography, printing, depositing nanoparticles onto the surface, and depositing microparticles onto the surface.

4. The method of claim 1, further comprising:
   depositing a magnetic material on the at least one material, where the depositing of the at least one material results in a structured surface with shapes that can be propelled at Reynolds numbers <1 by a rotation about the structure's long axis, and where said magnetic material is a ferromagnetic material.

5. The method of claim 1, wherein a magnetic material is subsequently added to the structures via a different deposition method comprising at least one of a surface functionalization method, chemical vapor deposition, thermal vapor deposition, sputtering, physical vapor deposition, and an electrochemical method.

6. The method of claim 1, wherein said MAPs are fabricated by evaporating material, with said material being magnetic, and wherein a non-magnetic material is subsequently added via a different deposition method comprising at least one of a surface functionalization method, chemical vapor deposition, thermal vapor deposition, sputtering, physical vapor deposition, and an electrochemical method.

7. The method of claim 1, wherein said MAPs are fabricated with a material comprising at least one of a magnetic material, a ferromagnetic material, and cobalt.

8. The method of claim 1, wherein said MAPs comprise a ferromagnetic material that is magnetized during or after fabrication.

9. The method of claim 1, wherein said MAPs are magnetically actuated in an environment comprising at least one of a fluid, a solution, a tissue, an organ, a gel, biological matter, a suspension, a cell, a cell culture, a plant, an animal, a human, soil, a solid, and a mixture, by the application of a magnetic field that comprises at least one of a homogenous magnetic field, a time-varying magnetic field, a magnetic field that changes its direction, and a magnetic field that has a gradient.

10. The method of claim 9, wherein said magnetic field used to actuate said MAPs changes in space to exert a torque on the MAPs, and where said magnetic field rotates in time and space and therefore causes the rotation of said MAPs, which due to their shape exhibit rotation-translation coupling and therefore translate through a medium in a desired direction.

11. The method of claim 9, wherein said magnetic field used to actuate the magnetic propellers is generated by manipulating permanent magnets.

12. The method of claim 9, wherein magnetic fields used to actuate the magnetic propellers are generated by passing current through an electric circuit comprising at least one of conductors, coils, Helmholtz coils, and Maxwell coils.

13. The method of claim 12, wherein said current is controlled by at least one of an electronic instrument, a computer, and a system with feedback control.

14. The method of claim 1, wherein at least one magnetically actuated propeller is used for at least one of: delivery of drug molecules, a contrast agent in medical imaging, delivery of materials that aid medical diagnosis, and delivery of materials that have therapeutic value.

15. The method of claim 1, wherein said MAPs are used to determine and/or measure a property comprising at least one of a rheological property and a mechanical property, in a medium comprising at least one of a fluid, a solution, a tissue, an organ, a gel, biological matter, a suspension, a cell, a cell culture, a plant, an animal, a human, soil, a solid, and a mixture.

16. The method of claim 1, wherein said MAPs are not actively propelled, but their passive thermal motion is observed with the aid of a device comprising at least one of a camera, a microscope, and an imaging device, and wherein said passive thermal motion is used to determine a mechanical or a rheological property comprising at least one of flow speed, flow direction, viscosity, elasticity, viscoelasticity, diffusion constant, and concentration.

17. The method of claim 1, wherein said magnetic propellers are used for sensing comprising at least one of: a pH level, an oxygen concentration, a sugar concentration, a gas concentration, a bio-molecule, a pathogen, a disease marker, a polynucleotide, a nucleic acid, a polypeptide, a protein, an antibody, a glycoprotein, a lipid, a carbohydrate, a fatty acid, a fatty ester, a macromolecular polypeptide complex, a vitamin, a virus, a bacterial cell, a virus infected cell, and a bacteria infected cell.

18. The method of claim 1, wherein said MAPs are coupled to a target comprising at least one of a biomolecule, a chemical, a pharmaceutical compound, a drug molecule, a nanoparticle, a quantum dot, a fluorescent molecule, an organic molecule, an inorganic molecule, and a part of the inorganic molecule, and wherein said MAPs are used to deliver said target to a desired location comprising at least one of a cell, a cell culture, a tissue, an organ, biological material, a fluid, a suspension, a liquid, a gel, a mixture, soil, inside a plant, inside an animal, inside a human, and inside a solid.

19. The method of claim 18, wherein said MAPs are used for an application used in at least one of biotechnology, veterinary medicine, diagnosis of human diseases, treatment of human diseases, and medicine.

20. The method of claim 18, wherein said biomolecule comprises at least one of a polynucleotide, a nucleic acid, a polypeptide, a protein, an antibody, a glycoprotein, a lipid, a carbohydrate, a fatty acid, a fatty ester, a macromolecular polypeptide complex, a vitamin, a virus, a bacterial cell, a virus infected cell, and a bacteria infected cell.

21. The method of claim 1, wherein at least one of said MAPs is employed to perform a task comprising at least one of entering, probing, and modifying, in a medium comprising at least one of a cell, a cell culture, a tissue, an organ, biological material, a fluid, a suspension, a liquid, a gel, a mixture, soil, a plant, an animal, a human, and a solid.

22. The method of claim 1, wherein said MAPs are made of at least one material that aids at least one of medical imaging, diagnosis, and medical therapy.

23. An apparatus for making magnetically actuated propellers (MAPs) configured to be moved by magnetic fields, comprising:

a vacuum chamber having at least one vapor source for generating a vapor flux, a substrate holder configured to hold a substrate onto which one or more materials from the at least one vapor source is deposited, and a means for controlling a deposition-rate of the vapor flux directed toward the substrate;

a process controller that controls a predetermined incidence angle theta formed by a direction of the vapor flux and a surface normal to the substrate, as well as a direction of rotation and a rotation speed of the substrate about an axis of the substrate during deposition, wherein the process controller is configured to adjust the rotation speed and the incidence angle in response to the deposition rate of the vapor flux, and the vapor flux is adjusted and the at least one source of the vapor flux is changed without breaking vacuum, the process controller being configured to generate commands to vary the incidence angle and the rotation speed during deposition so as to promote a growth of structures of a predetermined shape, and surface morphologies that, once removed from the substrate, permit propulsion of the structures in a medium by a magnetic field, the medium comprising at least one of a fluid, a solution, a tissue, an organ, a gel, biological matter, a cell, a cell culture, a suspension, soil, a plant, an animal, a human, a solid, and a mixture; and separation means for releasing the structures from the substrate, the separation means being configured to use a method comprising at least one of: sonication, vibration, agitation, dissolution, and etching.

24. The apparatus of claim 23, wherein the magnetically actuated propellers (MAPs) are fabricated by at least one of two-photon lithography, photolithography, interference lithography, stereolithography, lithographic techniques used for producing micro devices, focused ion beam etching, reactive ion etching, molecular beam epitaxy, chemical vapor deposition, emulsion polymerization, molding, laser cutting, printing, inkjet-printing, electrochemical deposition, physical vapor deposition, vacuum deposition, and Glancing Angle Deposition (GLAD).

* * * * *